United States Patent [19]
Bourgeois, Jr. et al.

[11] Patent Number: 5,667,524
[45] Date of Patent: Sep. 16, 1997

[54] THE E-Z DRAW CUFF

[76] Inventors: Ronnie J. Bourgeois, Jr.; Harry A. Oliver, Jr., both of P.O. Box 2033, Reserve, La. 70084

[21] Appl. No.: 661,642

[22] Filed: Jun. 11, 1996

[51] Int. Cl.⁶ .................................................. A61B 17/00
[52] U.S. Cl. ............................................................ 606/202
[58] Field of Search ........................ 606/191, 200–204; 128/667, 672, 677–679, 685

[56] References Cited

U.S. PATENT DOCUMENTS 3,929,129 12/1975 Archambault ........................ 606/202
5,201,758 4/1993 Glover ................................. 606/202
5,234,459 8/1993 Lee ..................................... 606/202
5,411,518 5/1995 Goldstein et al. .................. 606/202
5,413,582 5/1995 Eaton .................................. 606/202

*Primary Examiner*—Glenn Dawson
*Attorney, Agent, or Firm*—Patent & Trademark Services; Thomas Zack; Joseph H. McGlynn

[57] ABSTRACT

An inflatable medical cuff with a relief and safety valve. When the pressurized fluid from a pump exceeds a predetermined level, the safety valve pops-up to indicate the same. The relief valve may be used to reduce this excess pressure. A loop and hook fastener may be used to attach the cuff to a person's limb.

5 Claims, 1 Drawing Sheet

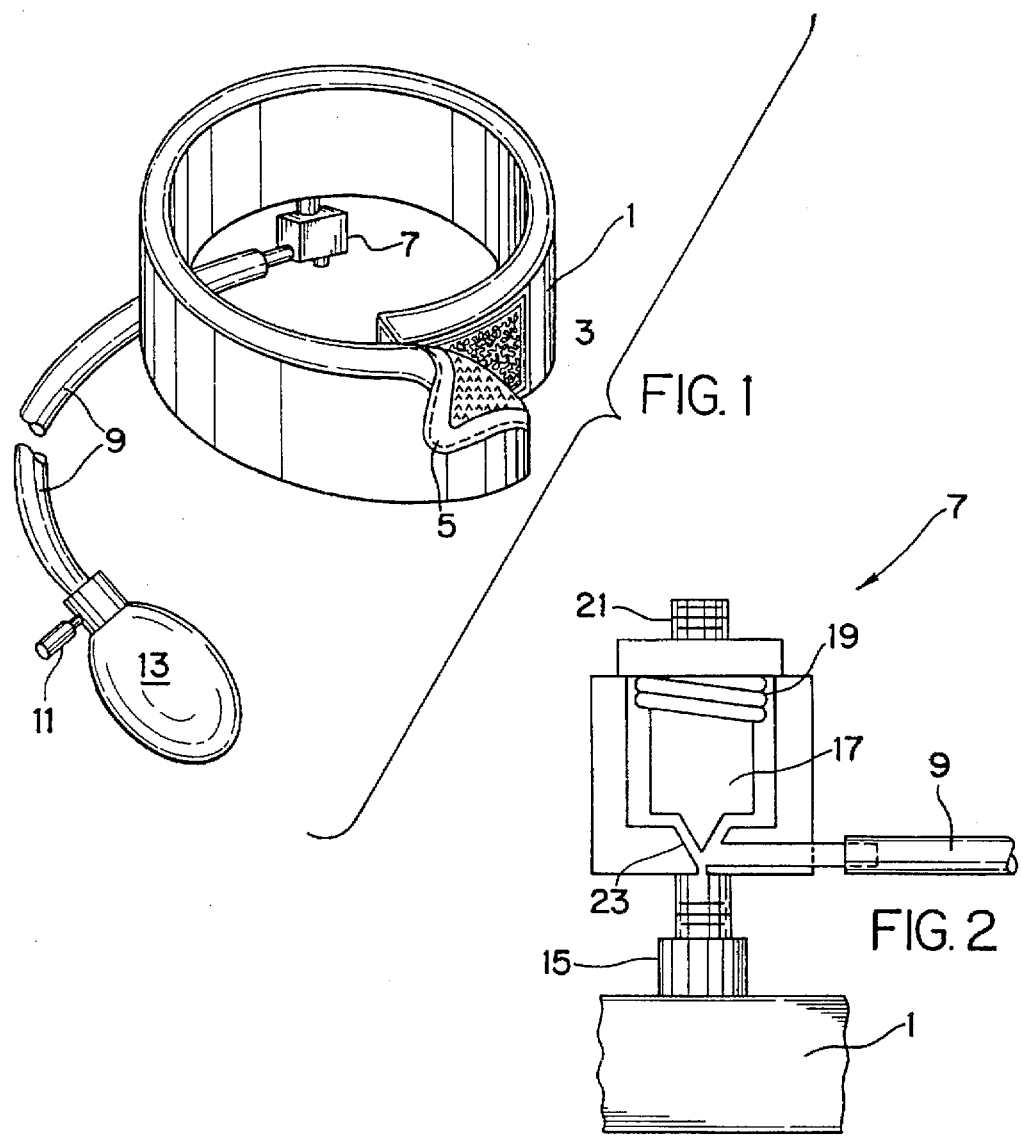
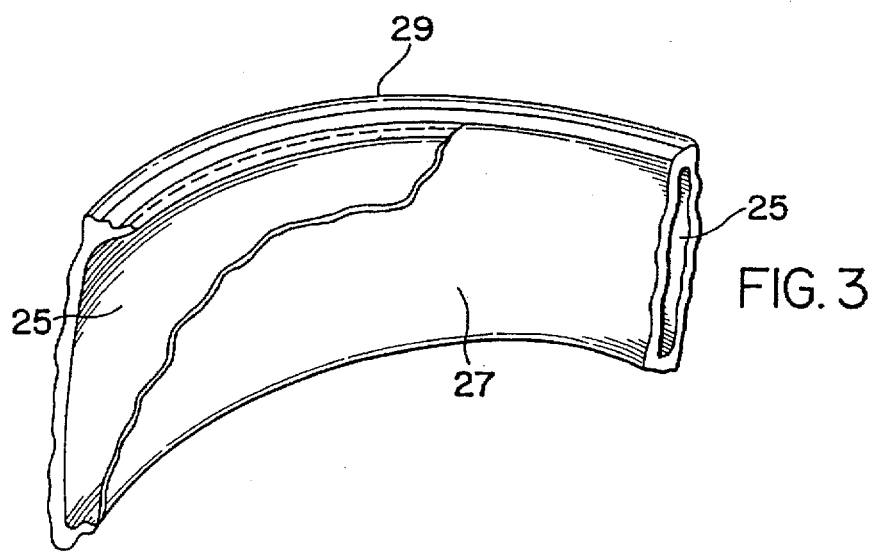

THE E-Z DRAW CUFF

BACKGROUND OF THE INVENTION

The present invention relates to an inflatable medical cuff used to apply pressure to a human limb. Should the pressure that is applied exceed an upper limit, a safety pop up valve is actuated to indicate the application of excessive pressure alerting a user to reduce the pressure.

DESCRIPTION OF THE PRIOR ART

In the prior art various types of tourniquet cuffs for reducing blood flow are disclosed. Many employ inflatable bladders and locking loops and hooks to hold the cuff to the person (U.S. Pat. No. 5,201,758 to Glover).

One is constructed with a pad between the tourniquet and person's body to reduce the patient's discomfort (U.S. Pat. No. 5,411,518 to Goldstein et al.).

Others uses different layer thickness in a disposable tourniquet (U.S. Pat. No. 5,413,582 to Eaton) or an adjustable strap with an inflatable balloon (U.S. Pat. No. 5,234,459 to Lee).

None of the known prior art employs a pop out safety valve to alert the user that a predetermined pressure has been exceeded.

SUMMARY OF THE INVENTION

The present invention consists of an inflatable medical cuff having an inflatable bladder, a pump ball with a release valve, and a safety valve. Pressures exceeding a safe level result in the safety valve popping up to indicate that the maximum safe inflation pressure has been reached.

It is an object of the present invention to provide an improved safety device for use with an inflatable medical tourniquet cuff.

It is a further object of the present invention to provide such a device wherein the user is visually alerted that a predetermined pressure level has been exceeded.

These and other objects and advantages of the present invention will be fully apparent from the following description, when taken in connection with the annexed drawings.

BRIEF DESCRIPTION OF THE DRAWINGS

FIG. 1 is a perspective view of the present invention.

FIG. 2 is a front view of the pressure relief valve used in the present invention.

FIG. 3 depicts the cuff with a section cut away to show its internal inflatable bladder.

DESCRIPTION OF THE PREFERRED EMBODIMENT

Referring now to the drawings in greater detail, FIG. 1 shows the components making up the preferred embodiment of my invention. The cuff 1 has an internal inflatable bladder (not shown), a fastening means 3 with a double layer fabric 5. In fluid communication with the cuff is a safety pop-up valve 7, the connecting hose 9 (shown with a section cut away), a pressure release valve 11 and the ball or bulb type pump 13. The fastening means can be a loop or hook member, such as found in a male and or female VELCRO hook and loop type material.

Initially the cuff is placed around a person's limb, such as an arm, and fastened with the fastener. Next, the ball or bulb pump 13 is pumped by hand resulting is pressurized air flowing from it through the hose and valve 7 to the cuff's internal inflatable bladder. Normally, the person is asked to make a tight fist when this occurs. As the bladder expands it restricts a person's blood flow at the cuff. This allows the drawing of blood for testing or to assist in the transmission of intravenous injections. Should the air pressure being applied to the inflatable bladder exceed a predetermined pressure level, usually about 65 pounds per square inch (PSI), the pop-up relief valve 7 is actuated.

FIG. 2 is illustrates a cut away view of the pop-up relief valve 7 to show its internal components in detail. Initially air flows to the valve via hose 9 and then through connection 15 to the cuff's internal bladder. This valve is made up of a needle valve 17 which reciprocates against a spring 19 which is attached to the excessive pressure pop-up indicator 21. When not pressurized, the needle valve rests in its valve seat 23. This pressure pop-up valve is a conventional spring loaded "needle valve" machined from stainless steel. As pressurized air flows from the pump the needle valve lifts from its seat and begins to compress the spring. When the compression becomes great enough, indicating excessive air pressure, the spring is compressed to the point where it overcomes the friction around the indicator and pops it up. Once, this happens the user is alerted that excessive pressure is present and may turn the relief valve 11 to reduce the pressure.

FIG. 3 illustrates the cuff and inflatable bladder with a section cut away to show its internal parts. The cuff 1 has an internal rubber bladder 25 in fluid communication with the valve 7, the hose 9, the pressure release valve 11 and the bulb type hand pump 13. As pressurized air is sent to the bladder it expands against the cuff's two layered fabric 5 with surfaces 27 and 29 between whom it is encased. In the preferred embodiment the fabrics surface of the cuff are made of a synthetic nylon or canvas material.

The rubber bladder can be manufactured in two ways rotational molding or vulcanization. With rotational molding plastisols and lattices are used in a hollow mold capable of being rotated in one or two planes. The hot mold fuses the plastic into a gel state after the rotation has caused it to cover all surfaces. The mold is then chilled and the product stripped out. With vulcanization a chemical reaction induces extensive changes in the physical properties of a rubber or plastic. Sulfur or other suitable agents are used in the reaction resulting in a decreased plastic flow, reduced surface thickness, increased elasticity, much greater tensile strength, and considerably less solubility. The bladder's construction used two sheets of rubber brought together under high heat and pressure in the perimeter area to be seamed. After a short period of time, the seam becomes vulcanized and can hold air. The rubber squeeze hand bulb pump 13 can also be manufactured using rotational molding techniques or purchased "off the shelf" in connection with the release valve.

Although the E-Z DRAW CUFF and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What we claim as our invention is:

1. An inflatable medical cuff comprising in fluid communication:

an inflatable bladder mounted in a medical cuff and adapted to supply pressure to the limb of a user;

a pressurized source of fluid in fluid communication with said bladder and adapted to supply pressurized fluid to the bladder;

a fluid release valve interposed between said pressurized source of fluid and bladder, said release valve being in fluid communication with said source and bladder; and a safety valve to visually indicate that the supplied fluid pressure to said bladder has exceeded a predetermined pressure level, said safety valve being in fluid communication with said pressurized source of fluid and said bladder.

2. The invention as claimed in claim 1, wherein said safety valve has a pop-up indicator to visually indicate that the applied fluid pressure has exceeded the predetermined level.

3. The invention as claimed in claim 2, wherein said pressurized source of fluid is a bulb pump.

4. The invention as claimed in claim 3, where said safety valve is a needle valve which acts against a spring attached to the indicator to move the pop-up indicator when the predetermined pressure level has been reached.

5. The invention as claimed in claim 1, also including hook and loop fastening means to attach said cuff to a person's limb.

* * * * *